(12) United States Patent
Ihle et al.

(10) Patent No.: US 9,242,020 B2
(45) Date of Patent: Jan. 26, 2016

(54) HEATING MODULE AND VAPORIZATION APPARATUS HAVING A HEATING MODULE

(75) Inventors: Jan Ihle, Grambach (AT); Werner Kahr, Deutschlandsberg (AT); Steffen Mehlig, Berlin (DE)

(73) Assignee: EPCOS AG (DE)

( * ) Notice: Subject to any disclaimer, the term of this patent is extended or adjusted under 35 U.S.C. 154(b) by 426 days.

(21) Appl. No.: 13/879,466

(22) PCT Filed: Oct. 11, 2011

(86) PCT No.: PCT/EP2011/067725
§ 371 (c)(1),
(2), (4) Date: Jun. 20, 2013

(87) PCT Pub. No.: WO2012/052321
PCT Pub. Date: Apr. 26, 2012

(65) Prior Publication Data
US 2013/0266297 A1    Oct. 10, 2013

(30) Foreign Application Priority Data

Oct. 18, 2010  (DE) .......................... 10 2010 048 779
Nov. 19, 2010  (DE) .......................... 10 2010 051 924
Feb. 18, 2011  (DE) .......................... 10 2011 011 692

(51) Int. Cl.

| | |
|---|---|
| *A01M 13/00* | (2006.01) |
| *F24F 6/00* | (2006.01) |
| *A61L 9/03* | (2006.01) |
| *A01M 1/20* | (2006.01) |
| *B01D 1/30* | (2006.01) |
| *H05B 3/14* | (2006.01) |
| *H05B 3/42* | (2006.01) |

(52) U.S. Cl.
CPC ............... *A61L 9/03* (2013.01); *A01M 1/2077* (2013.01); *A61L 9/037* (2013.01); *B01D 1/30* (2013.01); *H05B 3/14* (2013.01); *H05B 3/42* (2013.01); *H05B 2203/02* (2013.01); *H05B 2203/021* (2013.01); *H05B 2203/022* (2013.01)

(58) Field of Classification Search
None
See application file for complete search history.

(56) References Cited

U.S. PATENT DOCUMENTS

| | | | | |
|---|---|---|---|---|
| 4,489,232 | A | * | 12/1984 | Wada et al. .................. 219/206 |
| 4,874,924 | A |   | 10/1989 | Yamamoto et al. |
| 4,891,904 | A | * | 1/1990 | Tabita ............................ 43/112 |
| 5,401,935 | A | * | 3/1995 | Smith et al. .................. 219/206 |
| 6,411,776 | B1 | * | 6/2002 | Millan ........................... 392/395 |

(Continued)

FOREIGN PATENT DOCUMENTS

| | | |
|---|---|---|
| CN | 1030508 | 1/1989 |
| CN | 2229264 | 6/1996 |

(Continued)

OTHER PUBLICATIONS

English translation of corresponding Office Action of CN Application No. 201180050308.1 dated Dec. 3, 2014.

(Continued)

*Primary Examiner* — Thor Campbell
(74) *Attorney, Agent, or Firm* — DLA Piper LLP (US)

(57) ABSTRACT

A heating module includes a housing with an opening, and a PTC ceramic heating element arranged in the housing having an inner face facing toward the opening, an outer face facing away from the opening and two end faces connecting the inner and outer faces, wherein the inner face is at least partially matched to the opening.

16 Claims, 7 Drawing Sheets

(56) References Cited

U.S. PATENT DOCUMENTS

| | | | |
|---|---|---|---|
| 6,697,571 B2 * | 2/2004 | Triplett et al. | 392/395 |
| 8,027,575 B2 * | 9/2011 | Hasik et al. | 392/394 |
| 8,666,236 B2 * | 3/2014 | Miguens et al. | 392/395 |

FOREIGN PATENT DOCUMENTS

| | | |
|---|---|---|
| CN | 101854748 | 10/2010 |
| EP | 0 290 159 A2 | 11/1988 |
| EP | 0 689 766 A1 | 1/1996 |
| JP | 05-284889 | 11/1993 |
| JP | 08-045705 | 2/1996 |
| JP | 8-255676 | 10/1996 |
| JP | 10-075996 A | 3/1998 |
| JP | 10-172804 | 6/1998 |
| JP | 10-263066 A | 10/1998 |
| JP | 2002-501392 | 1/2002 |
| JP | 2005-116585 | 4/2005 |

OTHER PUBLICATIONS

Japanese Office Action dated Mar. 18, 2014 with partial English translation from corresponding Japanese Application No. 2013-534428.

* cited by examiner

HEATING MODULE AND VAPORIZATION APPARATUS HAVING A HEATING MODULE

TECHNICAL FIELD

This disclosure relates to a heating module and a vaporization apparatus having a heating module.

BACKGROUND

Heating systems that vaporize fluids containing aromatic substances or active substances, for example, for repelling insects such as mosquitoes, are known. Such fluids containing an active substance are vaporized, for example, with a wick which protrudes out of a container filled with the fluid and heated by a heating unit positioned at the end of the wick.

PTC heating elements are used predominantly for heating systems that vaporize fluids containing an active substance. In that case, heating is usually effected by planar PTC heating elements, in particular by PTC heating elements formed as disks or rectangular elements and arranged between contact plates in a housing made of plastic or ceramic.

To generate the heat required for vaporization, an appropriately high temperature has to be achieved at the wick, there being no direct contact for a good heat transfer on account of an annular gap, which is required to form convection action, between the wick and the heating unit. In the majority of cases, heat generated by a PTC heating element is transferred to a heat conductor, which can surround the wick and which can in turn heat the wick. As a result, it is necessary to heat the PTC heating element to a temperature which lies considerably above the temperature required for vaporization at the wick.

The disadvantage of the current applications is, therefore, a low degree of efficiency on account of the unfavorable surface-to-volume ratio of the PTC ceramic and the arrangement of the PTC heating element at a great distance from the actual heat transfer surface. This usually has the effect that considerably higher heating powers have to be provided and/or compromises are necessary in the structural design.

It could therefore be helpful to provide a heating module and a vaporization apparatus having a heating module.

SUMMARY

We provide a heating module including a housing with an opening, and a PTC ceramic heating element arranged in the housing and having an inner face facing toward the opening, an outer face facing away from the opening and two end faces connecting the inner and outer faces, wherein the inner face is at least partially matched to the opening.

We also provide a vaporization apparatus including a container, a liquid-conducting element and the heating module, wherein the liquid-conducting element protrudes into the heating module with one end and into the container with the other end.

LIST OF REFERENCE SIGNS

1 Heating module
2 PTC ceramic heating element
21 Inner face
22 Outer face
23, 24 End face
3 Housing
31 Opening
32, 33 Housing part
34 Inner space
41, 42, 43 Contact element
44 Connecting lug
5 Inner sleeve
6 External diameter of the PTC ceramic heating element
7 Height of the PTC ceramic heating element
8 Angle
9 Beveled region
91 Length of the beveled region
10 Vaporization apparatus
11 Container
12 Liquid-conducting element
13 Holding device

DETAILED DESCRIPTION

Our heating module may have a housing with an opening and a PTC ceramic heating element arranged in the housing. The PTC ceramic heating element has an inner face facing toward the opening, an outer face facing away from the opening and two end faces connecting the inner and outer faces. Furthermore, the inner face of the PTC ceramic heating element is at least partially matched to the opening.

The shape of the PTC ceramic heating element may be matched to the shape of the opening. It is preferable in particular that the overall shape of the inner face of the PTC ceramic heating element facing toward the opening is matched to the shape of the opening. In particular, the inner face of the PTC ceramic heating element has a curved surface which at least partially encompasses the opening in the housing. The surface of the inner face preferably has an arcuate cross section.

The heating module can be configured in particular to heat a liquid-conducting element, for example, a wick or a capillary, or can be used for that purpose.

By way of example, the liquid-conducting element can be guided through the opening in the housing. The heating module is preferably configured such that the PTC ceramic heating element is arranged close to the opening. The PTC ceramic heating element in this case at least partially encompasses the wick. It is advantageously possible to thereby dispense with further elements for heat conduction between the PTC ceramic heating element and the liquid-conducting element such that the liquid-conducting element can be heated directly by the PTC ceramic heating element.

The PTC ceramic heating element may comprise a functional ceramic, for example, based on $BaTiO_3$, which can be produced, for example, by pressing technology or injection molding technology.

The PTC ceramic heating element may have electrodes at the end faces thereof. The electrodes are formed, for example, by metallizations applied to the PTC ceramic heating element. The electrodes serve for the electrical contact-connection of the PTC ceramic heating element.

A contact element may be arranged on each of the end faces of the PTC ceramic heating element. The contact elements can be in the form of contact plates, for example. The contact elements may comprise aluminum or consist of aluminum. The contact elements preferably comprise pure aluminum, for example, that with the designation EN AW-Al 99.5 (3.0255), or consist of this material.

The PTC ceramic heating element may be arranged between the contact elements by a clamping contact-connection. The PTC ceramic heating element is preferably fastened between the contact elements by clamping. The clamping contact-connection between the contact elements and the PTC ceramic heating element does not require any spring elements, but instead the contact elements, the PTC ceramic heating element and the housing can be configured such that a mechanical force is exerted on the contact elements and the PTC ceramic heating element, by which the contact elements and the PTC ceramic heating element are pressed against one another and thus clamped.

The shape of the contact elements may at least be partially matched to the shape of the PTC ceramic heating element.

The contact elements may be formed at least partially with an annular shape or U shape.

Furthermore, the contact elements can have a frustoconical shape or a frustoconical region matched to a conical shape of the PTC ceramic heating element at the end faces thereof. Similarly, the housing can have corresponding conical regions by way of which, in the assembled state, the contact elements are pressed with the respective frustoconical region against the conical end faces of the PTC ceramic heating element.

The heating module may have three contact elements. The contact elements are preferably matched to the shape of the PTC ceramic heating element. By way of example, two of the three contact elements can be arranged on one end face of the PTC ceramic heating element and one contact element can be arranged on the other end face of the PTC ceramic heating element. In this respect, on one end face the PTC ceramic heating element can have two separate electrodes, each realized by metallizations on the end face and are separate from one another. The heating module can therefore be configured such that it has three separate connections.

The end faces of the PTC ceramic heating element may at least be partially beveled. The clamping action between the PTC ceramic heating element and the contact elements in the housing can be improved further by the at least partially beveled end faces.

The PTC ceramic heating element may be formed with an annular shape. The PTC ceramic heating element can in particular have an opening preferably matched in terms of its shape and its size to the opening in the housing. It is thereby possible for heat transfer between the PTC ceramic heating element and a liquid-conducting element arranged in the opening in the housing to be improved.

The PTC ceramic heating element may be formed at least partially conically on the end faces. By way of example, the end faces of the PTC ceramic heating element have conical regions, which can also be referred to as so-called "phases." The clamping contact-connection between the PTC ceramic heating element and the contact elements can be improved by the conical formation of the end faces. The end faces of the PTC ceramic heating element are preferably beveled in the direction of the outer face.

The PTC ceramic heating element may be formed with a U shape or horseshoe shape. Owing to the U-shaped configuration of the PTC ceramic heating element, the latter can at least partially encompass the liquid-conducting element, for example, a wick or a capillary. The PTC ceramic heating element is therefore located in the immediate vicinity of the liquid-conducting element as a result of which the heat transfer from the PTC ceramic heating element to the liquid-conducting element can be improved.

The PTC ceramic heating element may have a smaller height on the inner face facing toward the opening than on the outer face facing away from the opening. By way of example, the PTC ceramic heating element can be formed with a wedge shape as seen from a central point of the opening.

Furthermore, the housing can have an inner space having a wedge-shaped cross section. The wedge shape is preferably tapered radially inward, i.e., in the direction of the opening.

The wedge shape of the inner space of the housing and the shape of the PTC ceramic heating element may be matched to one another. If the housing is closed, the PTC ceramic heating element slides into a position in which it is clamped in between the contact elements and the housing. This ensures that there is a permanent clamping contact-connection between the PTC ceramic heating element and the contact elements in the housing.

The housing may comprise at least two housing parts connected to one another by a latching connection. A mechanical force is exerted on the contact elements arranged in the housing and on the PTC ceramic heating element by the latching connection of the housing parts such that the contact elements and the PTC ceramic heating element are clamped to one another.

Instances of mechanical damage to the PTC ceramic heating element resulting from the different thermal expansions of the materials can be avoided by a permanent clamping contact-connection and the associated compressive stress in the ceramic.

The at least two housing parts may connect to a flanged inner sleeve. The inner sleeve preferably comprises metal. Furthermore, it is preferable for the inner sleeve to be arranged at least partially in the opening in the housing. It can be flanged during assembly, for example, and can thereby bring about permanent clamping of the housing and of the PTC ceramic heating element.

The housing parts may comprise a plastic. The housing or the housing parts can comprise, for example, polybutylene terephthalate (PBT) or liquid crystal polymer (LCP). Furthermore, the housing parts can be designed to electrically insulate the inner sleeve such that the PTC ceramic heating element is separated by an inner shell. In other words, the housing can have a wall or a wall region encompassing the opening between the inner face of the PTC ceramic heating element and the opening.

The contact elements may have connecting lugs protruding out of the housing for the electrical contact-connection. Furthermore, the connecting lugs can be designed such that commercially available flat connectors can be connected.

Crimp connections, for example, can be provided for the electrical contact-connection to the contact elements.

In the case of the heating module described here, the transfer of heat from the PTC ceramic heating element to the liquid-conducting element is effected with a high degree of efficiency. Furthermore, the PTC ceramic heating element is advantageously distinguished by a favorable surface-to-volume ratio.

A vaporization apparatus may have a container, a liquid-conducting element and a heating module according to one or more of the aforementioned examples. In this case, the liquid-conducting element protrudes into the heating module with one end. In this region, the liquid-conducting element is preferably surrounded at least partially by the PTC ceramic heating element such that the best possible heat transfer can be effected between the PTC ceramic heating element and the liquid-conducting element. With the other end, the liquid-conducting element protrudes into the container which can be filled at least partially with a liquid, preferably with a fluid containing an active substance, for example, a liquid containing natural pyrethrum, pyrethroids or essential oils to repel mosquitoes. Alternatively, liquids that improve the room air, so-called "air fresheners," may also be involved.

By way of example, the liquid containing, for example, one of the aforementioned active substances can be vaporized using a vaporization apparatus described here to repel insects or improve the room air.

Further advantages of the heating module become apparent from the examples described hereinbelow in conjunction with FIGS. 1 to 12.

Figure 1:
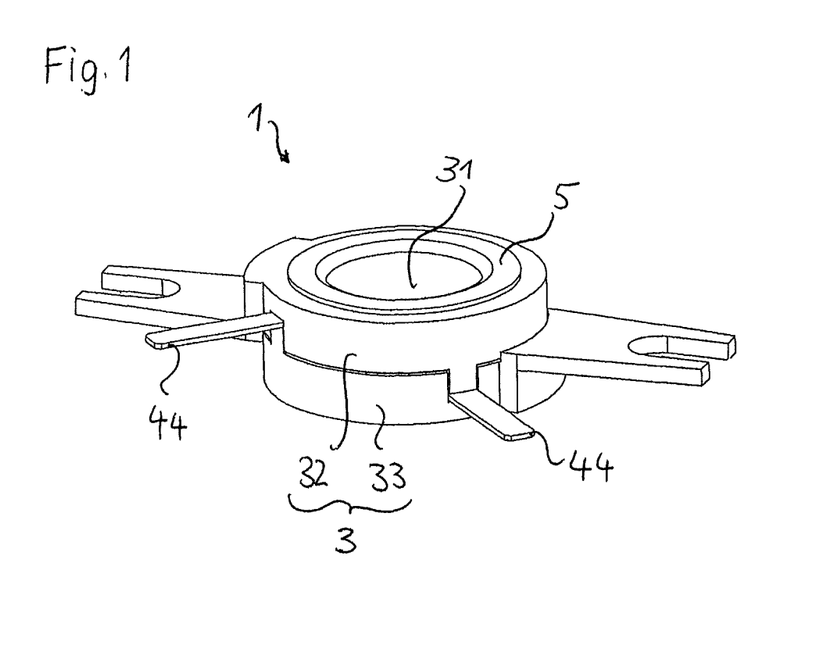
FIGS. 1 to 5 are illustrations of a heating module and also elements of the heating module according to one example.
Figure 2:
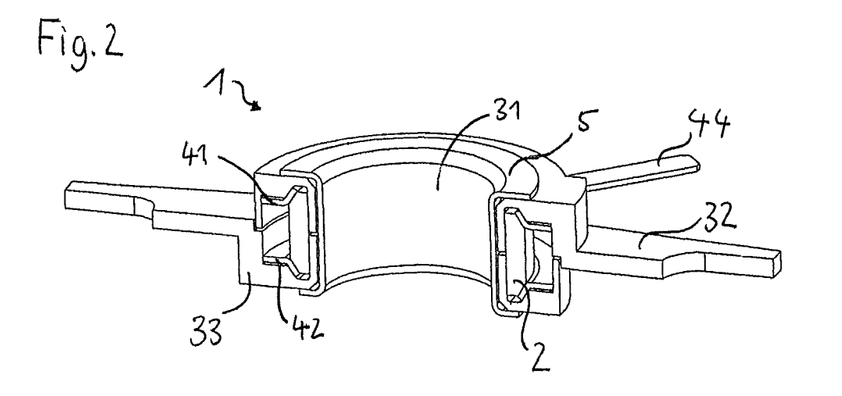
Figure 3:
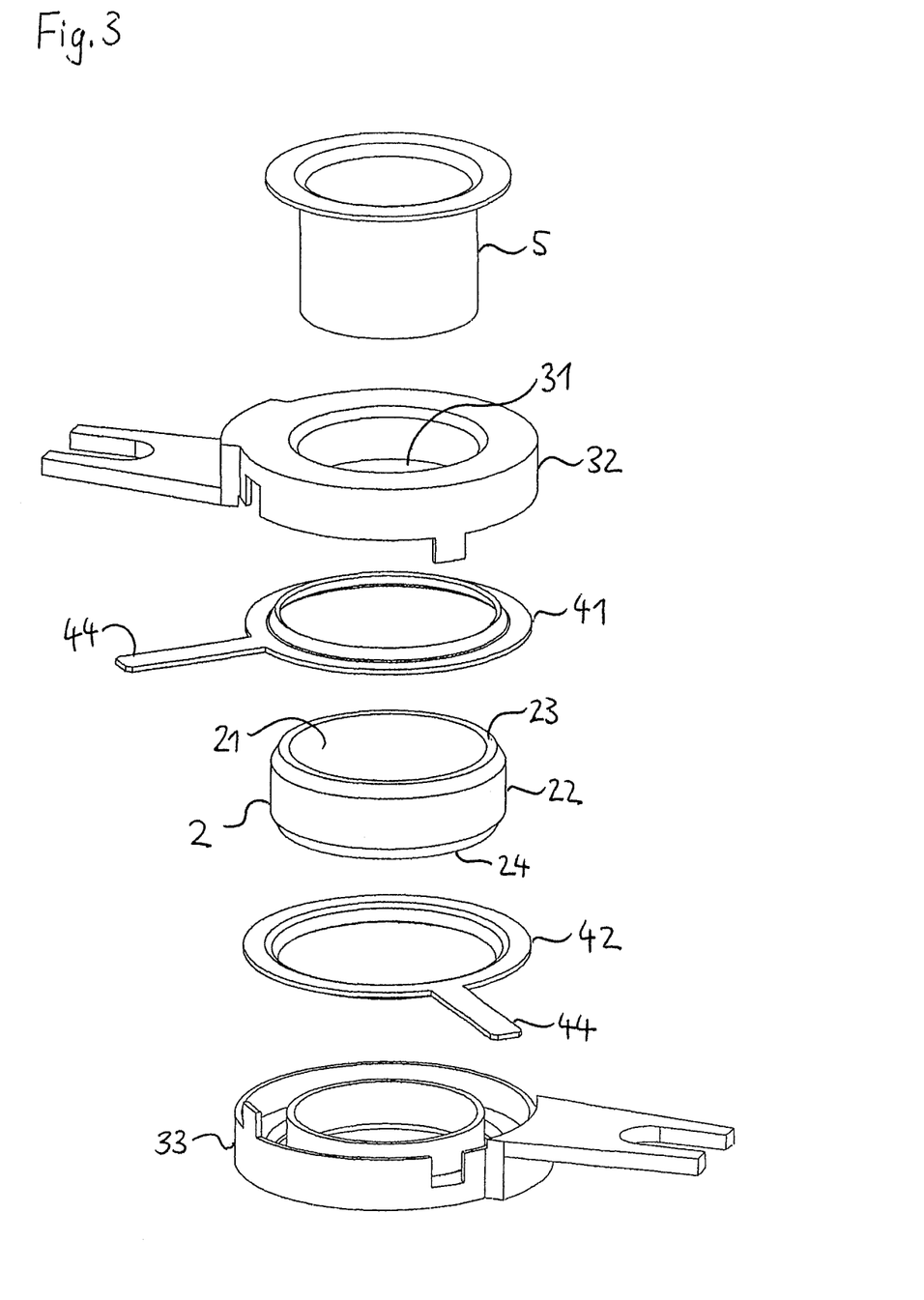

FIGS. 1 to 5 show schematic views of a heating module 1 and also of components thereof according to a first example. FIG. 1 shows the heating module 1 in this case in an assembled state, whereas FIG. 2 shows a schematic view of the cut-through heating module 1 shown in FIG. 1. FIG. 3 shows the heating module 1 shown in FIG. 1 in the form of an exploded illustration.

The heating module 1 shown is designed as an annular heating module and has a housing 3 with an opening 31 and a PTC ceramic heating element arranged in the housing 3. The opening 31 is formed with a circular shape and can receive, for example, a liquid-conducting element such as a wick or a capillary.

The housing 3 comprises two housing parts 32, 33. The housing parts 32, 33 each have holding arms extending radially away from the opening 31 and, at the end, each have a U-shaped region. The heating module 1 can thereby be fastened to a holding device, for example.

The PTC ceramic heating element 2 is formed with an annular shape and thus encompasses the opening 31 in the housing 3. Between the PTC ceramic heating element 2 and the opening 31, each of the housing parts 31, 32 has a wall region, by which the PTC ceramic heating element 2 is isolated from the opening 31 and an inner sleeve 5 (described further hereinbelow) arranged in the opening 31. The end faces of the PTC ceramic heating element 2 are beveled in the direction of the outer face, as a result of which the PTC ceramic heating element 2 obtains a conical shape at the end faces.

Figure 4:
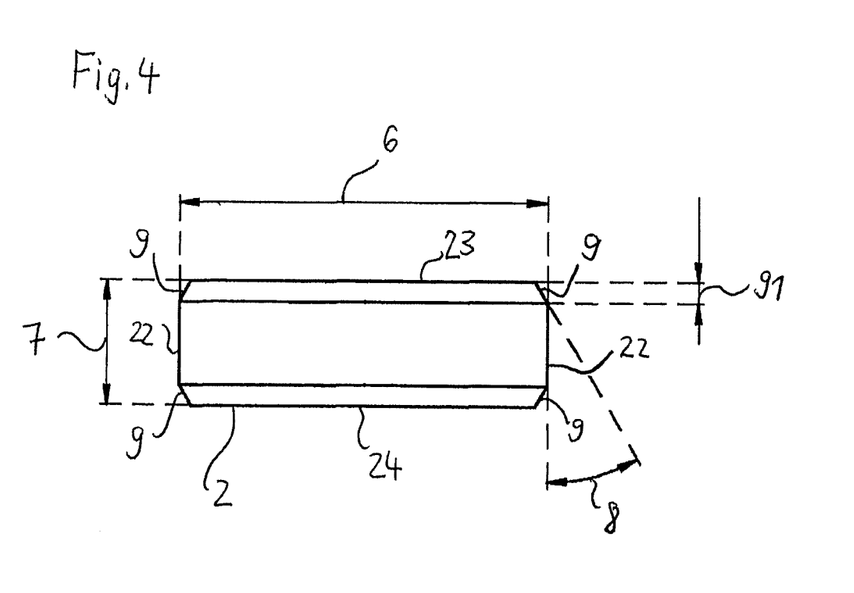

FIG. 4 shows the PTC ceramic heating element 2 in a side view. The beveled end faces 23, 24 include an angle 8 of purely by way of example 30° with the outer face 22. The beveled end faces 23, 24 have beveled regions 9 which, for example, have a length of 0.75 mm in the direction of the opening axis of the PTC ceramic heating element 2. The wall thickness of the PTC ceramic heating element 2 is approximately 1 mm. Alternatively, the wall thickness of the PTC ceramic heating element 2 is 0.5 mm to 2.5 mm. The external diameter 6 of the PTC ceramic heating element 2 is purely by way of example 13.26 mm. Furthermore, the PTC ceramic heating element 2 has purely by way of example a height 7 of 4.5 mm.

Electrodes via which electrical contact can be made with the PTC ceramic heating element 2 are applied to the beveled regions 9 of the end faces 23, 24.

Electrical contact is made with the PTC ceramic heating element 2 by conical clamping via two contact elements 41, 42 arranged on the end faces 23, 24. The contact elements 41, 42 are each formed as a frustoconical contact ring with a connecting lug 44.

Figure 5:
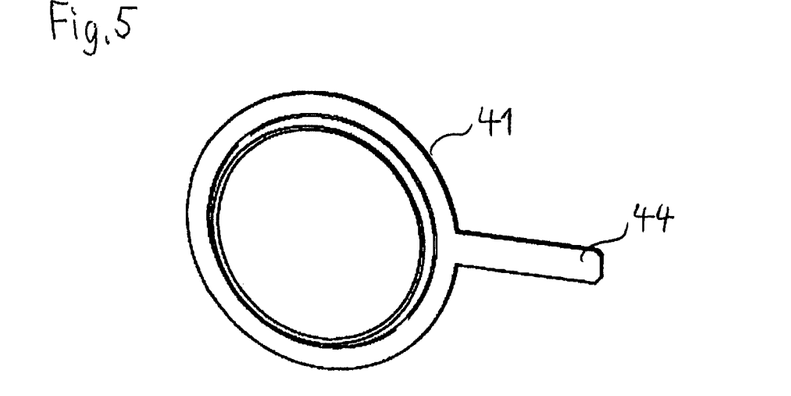

FIG. 5 shows, for clarification, a schematic view of the contact element 41.

The contact elements 41, 42 are matched in terms of their shape to the PTC ceramic heating element 2, as a result of which a positively fitting connection can be achieved between the contact elements 41, 42 and the PTC ceramic heating element 2. In particular, the PTC ceramic heating element 2 is fastened between the contact elements 41, 42 by a clamping contact-connection. The clamping is effected by the conical end faces 23, 24 onto which the two contact elements 41, 42 are pressed. To this end, in the regions which adjoin the contact elements 41, 42 in the region of the end faces 23, 24 of the PTC ceramic heating element 2, the housing parts 31, 32 likewise have conical surfaces, by way of which the contact elements 41, 42 are pressed against the end faces 23, 24 when the housing 3 is in the closed state.

A metal sleeve 5 arranged in the opening 31 and preferably flanged during assembly, ensures that there is permanent clamping since the two housing parts 32, 33, which, in the region in which the contact elements 41, 42 are seated, have the same conical shape as the contact elements 41, 42 and the PTC ceramic heating element 2, are pressed together by the metal inner sleeve 5 during flanging.

The exploded illustration in FIG. 3 shows the individual components of the heating module 1 one above another such as the inner sleeve 5, the housing parts 32 and 33, the contact elements 41 and 42 and also the PTC ceramic heating element 2, for clarification. In particular, it can be seen that the PTC ceramic heating element 2 is matched to the shape of the opening 31 in terms of the shape of its inner face 21 facing toward the opening 31. Furthermore, it is possible to identify the beveled end faces 23, 24 of the PTC ceramic heating element 2 and also the frustoconical contact elements 41, 42 matched in terms of their shape to the PTC ceramic heating element 2.

The inner sleeve 5 and/or one or both of the contact elements 41, 42 can comprise, with particular preference, aluminum, for instance pure aluminum, for example, that with the designation EN AW-Al 99.5 (3.0255), or consist thereof. The inner sleeve 5 has, for example, a mass of approximately 0.3 g, and the contact elements 41, 42 each have, for example, a mass of approximately 0.1 g. The housing parts 32, 33 can comprise, for example, plastic materials, for example, polybutylene terephthalate (PBT) or liquid crystal polymer (LCP). The housing parts 32, 33 have, for example, a mass of approximately 0.4 g.

The diameter of the heating module 1 is adapted for the corresponding application and, in the example shown, is approximately 20 mm. Alternatively, the diameter of the heating module 1 can be 1 mm to 50 mm.

The height of the heating module 1 is approximately 6.8 mm. Alternatively, depending on the requirement, the height of the heating module 1 can vary between 2 mm and 20 mm. Longer heating modules are conceivable, but depending on the requirement primarily those of up to 20 mm can prove to be particularly advantageous.

The heating module 1 described here represents a cost-effective and efficient heating arrangement which, on the one hand, generates heat completely over the entire circumference without additional electronic control of the heating power and, on the other hand, has a clamping contact-connection without spring elements.

Figure 6:
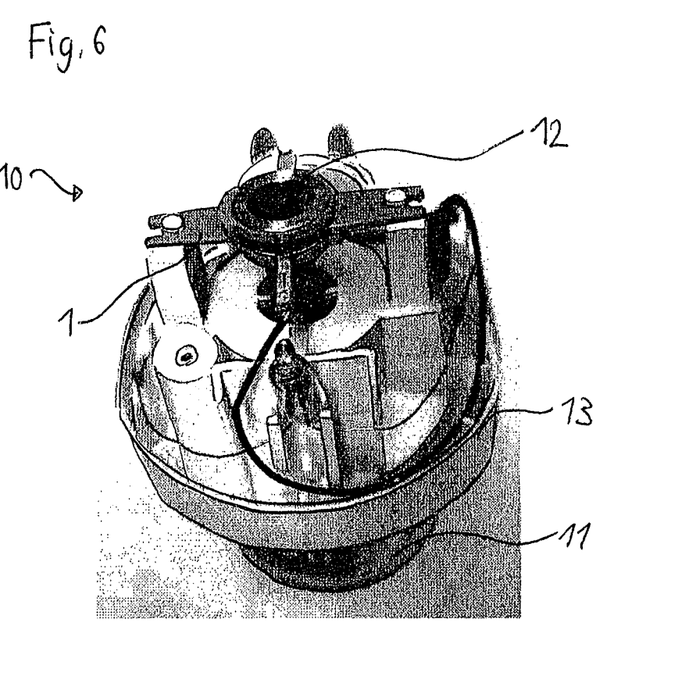
FIGS. 6 and 7 show a vaporization apparatus according to a further example.
Figure 7:
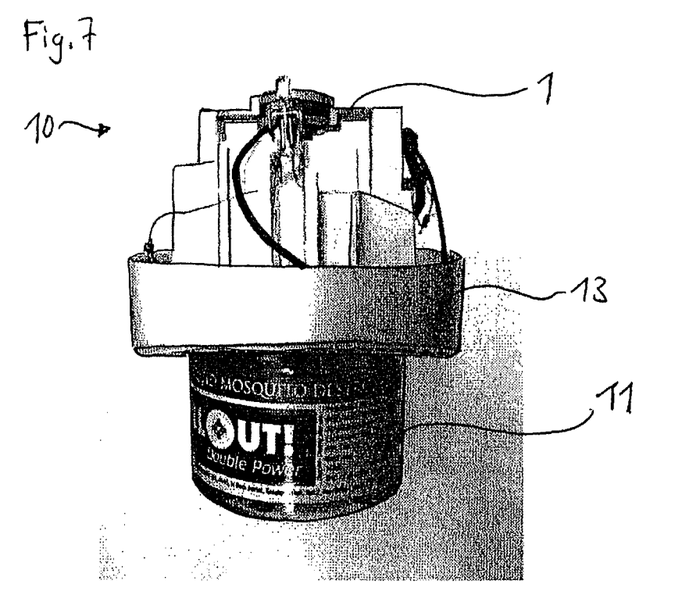

FIGS. 6 and 7 show a vaporization apparatus 10 according to a further example, which comprises a heating module 1, a liquid-conducting element 12 and a container 11. The heating module 1 is formed here essentially like the heating module according to the example shown in FIGS. 1 to 5.

The container 11 has a holding device 13 on which the heating module 1 is fastened. To this end, the holding device 13 has two nipples on which the housing of the heating module 1 is fastened by clamping.

The liquid-conducting element 12 is designed as a wick. Alternatively, the liquid-conducting element 12 can also be designed as a capillary. The liquid-conducting element 12 protrudes into the heating module 1 with one end and in this region is surrounded at least partially by the PTC ceramic heating element arranged in the heating module 1. With the other end, the liquid-conducting element 12 protrudes into the container 11 which is filled at least partially, for example, with a liquid containing natural pyrethrum, pyrethroids or essential oils that repel mosquitoes. Alternatively, a liquid that improves the room air may also be involved. The diameter and/or the structure of the liquid-conducting element 12 is preferably selected such that a fluid present in the container 11 can rise up to the PTC ceramic heating element.

The fluid is conducted to the heating module 1 and therefore to the PTC ceramic heating element by a capillary force in the liquid-conducting element 12, for example, and vaporized by the action of heat.

The vaporization apparatus 10 described here has a very high degree of efficiency combined with a relatively low electrical power consumption since the heat required for vaporization is generated very close to and, in the example shown, around the entire liquid-conducting element 12.

Figure 8:
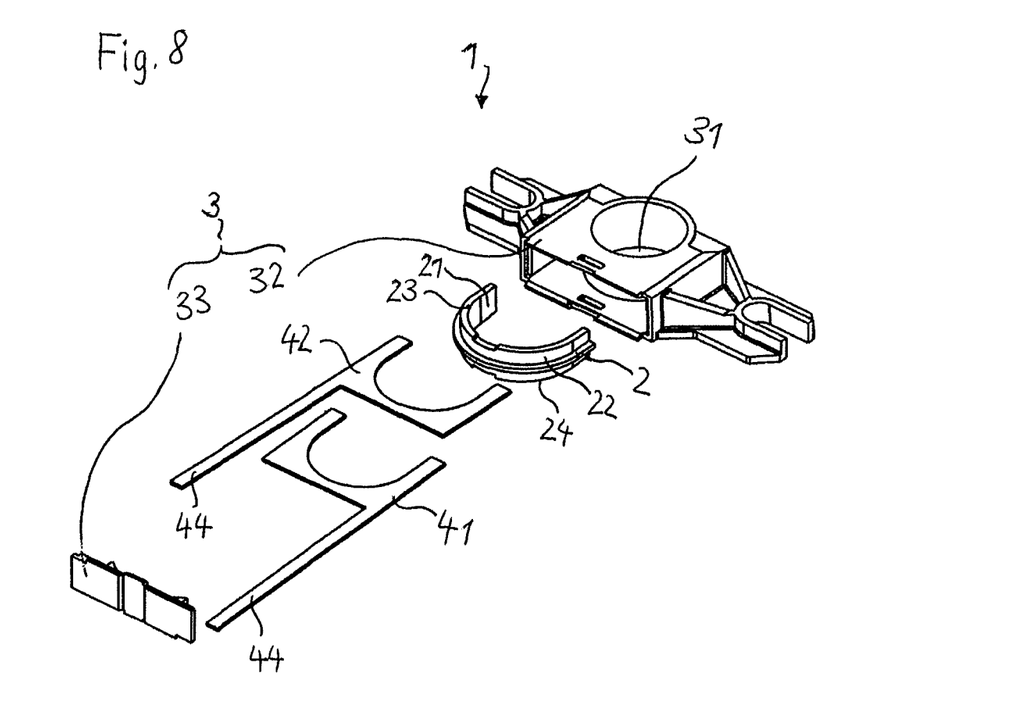
FIGS. 8 to 10 are illustrations of a heating module according to a further example.
Figure 9:
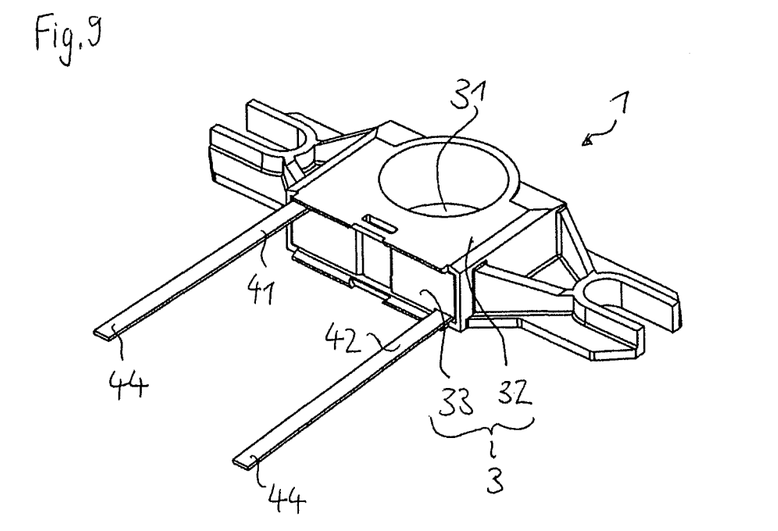
Figure 10:
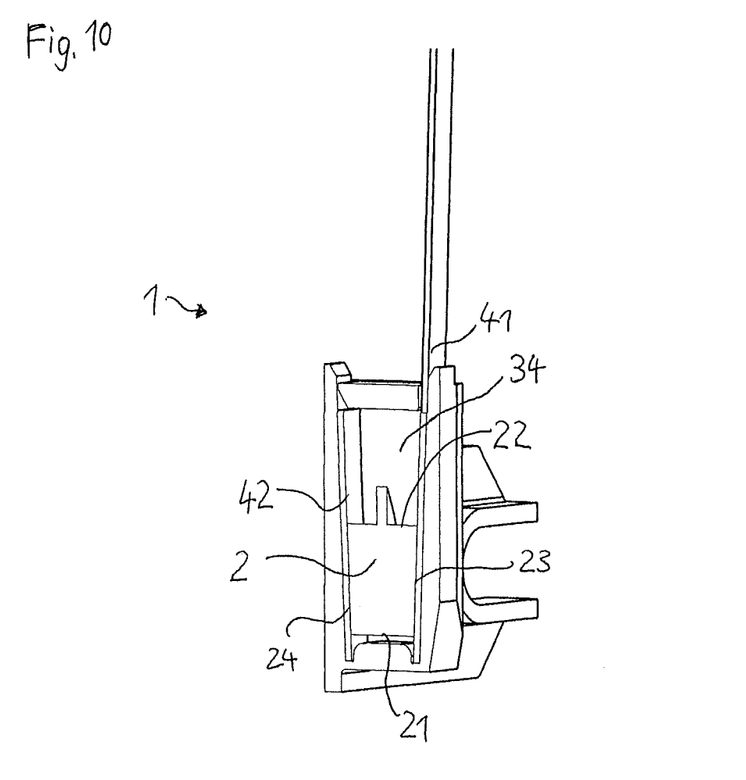

FIGS. 8 to 10 show a heating module 1 according to a further example, FIG. 8 showing an exploded illustration of the heating module 1, FIG. 9 showing a schematic view of a closed heating module 1 and FIG. 10 showing a cut-through heating module 1.

The heating module 1 has a two-part housing 3. The housing 3 comprises the housing parts 32, 33. In this case, the housing part 32 is formed as the housing body and the housing part 33 is formed as the housing cover. The housing body 32 forms the bottom side, the top side and three side faces of the housing 3. When the housing 3 is in the closed state, the housing cover 33 forms the fourth side face of the housing 3. Furthermore, the housing 3 has U-shaped assembly arms, by which the heating module 1 can be fastened.

The housing cover 33 and the housing body 32 can be produced separately or alternatively also in a common injection molding process and, in the latter case, are connected to one another at one location by a so-called "film gate," this connection being unstable and fragile. In a subsequent assembly step, the housing cover 33 is detached from the housing body 32. To close the housing, the housing cover 33 can then be latched to the housing body 32, the housing cover 33 and the housing body 32 being connected to one another by way of a latching connection.

The housing 3 or the housing body 32 has a continuous opening 31 in the center of both the top side and the bottom side. If the heating module 1 is used to heat a liquid-conducting element, the liquid-conducting element can be guided through the opening 31.

The heating module 1 has a U-shaped PTC ceramic heating element 2. The end faces 23, 24 of the U-shaped PTC ceramic heating element are beveled. In the section through the heating module 1 as shown in FIG. 10, it can be seen that the PTC ceramic heating element 2 has a smaller height on the inner face 21 facing toward the opening than on the outer face 22 facing away from the opening. Therefore, the PTC ceramic heating element is formed with a wedge-shaped cross section, tapering toward the inner face 21.

Furthermore, the housing 3 has an inner space 34. The inner space 34 can taper, for example, in the direction of the opening 31 in the housing 3. The tapered formation of the housing 2 is preferably matched to the tapered formation of the PTC ceramic heating element 2. By way of example, both of the tapered formations can be made at the same angle. If the housing 3 is closed, the PTC ceramic heating element 2 slides into a position in which it is clamped in in the housing 3.

The PTC ceramic heating element 2 has electrodes on its two end faces 23, 24. These are formed by metallizations applied to the ceramic.

On the outer face 22, the PTC ceramic heating element 2 has a fin, which serves substantially to mechanically stabilize the PTC ceramic heating element 2.

By virtue of the U-shaped configuration of the PTC ceramic heating element 2, the latter can at least partially encompass a wick. The PTC ceramic heating element 2 is, therefore, in the immediate vicinity of the wick as a result of which the transfer of heat from the PTC ceramic heating element 2 to the wick can be effected with a high degree of efficiency.

Furthermore, the heating module 1 has two contact elements 41, 42. The first contact element 41 is arranged along the opening axis under the PTC ceramic heating element 2 and the second contact element 42 is arranged above the PTC ceramic heating element 2. Accordingly, the first contact element 41 bears against the end face 23 of the PTC ceramic heating element 2. The second contact element 42 bears against the second end face 24 of the PTC ceramic heating element 2.

The contact elements 41, 42 are designed in flat form and matched to the shape of the PTC ceramic heating element 2. Accordingly, the contact elements 41, 42 have a U-shaped recess. Furthermore, the contact elements 41, 42 have connecting lugs 44, which serve for the electrical contact-connection of the contact elements 41, 42 and, therefore, also for the electrical contact-connection of the PTC ceramic heating element 2, which, when the housing 3 is closed, is electrically conductively connected to the contact elements 41, 42.

If the housing 3 is closed, i.e., if the housing cover 33 is latched to the housing body 32, the PTC ceramic heating element 2 and the contact elements 41, 42 are pressed into the housing 3. The contact elements 41, 42 and the PTC ceramic heating element 2 are thereby clamped to one another. The contact elements 41, 42 and the PTC ceramic heating element 2 electrically connect to one another by this clamping contact-connection.

No spring element whatsoever is required for the clamping contact-connection between the contact elements 41, 42 and the PTC ceramic heating element 2. Instead, the housing 3 can be configured such that, when the housing 3 is in the closed state, a mechanical pressure is exerted on the contact elements 41, 42 and the PTC ceramic heating element 2, by which the contact elements 41, 42 and the PTC ceramic heating element 2 are pressed together and thus clamped. By way of example, when the housing 3 is being closed, the PTC ceramic heating element 2 can slide into a position in which it is clamped in between the contact elements 41, 42 and the housing 3.

By way of example, the clamping contact-connection realized by way of the wedge shape of the PTC ceramic heating element 2 and the housing 3 and the accompanying compressive stress in the ceramic can prevent instances of mechanical damage to the PTC ceramic heating element 2 resulting from different thermal expansions of the various materials.

Figure 11:
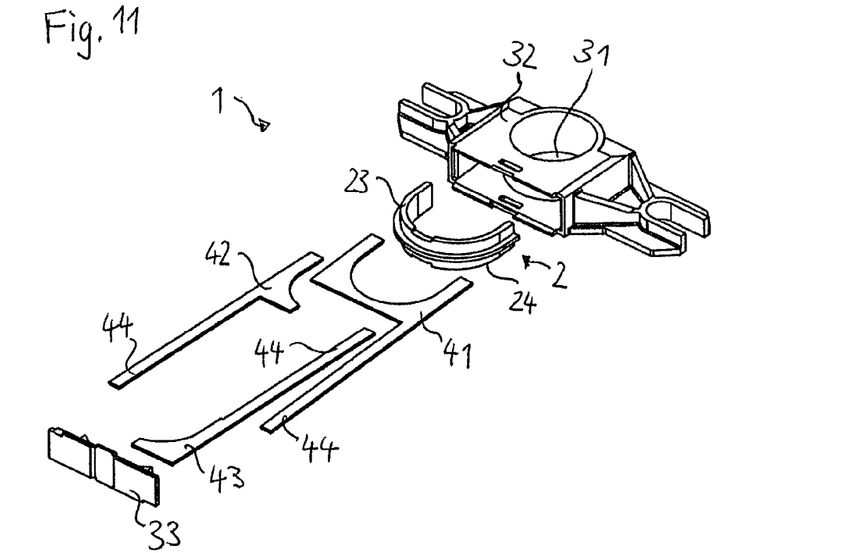
FIGS. 11 and 12 are illustrations of a heating module according to a further example.
Figure 12:
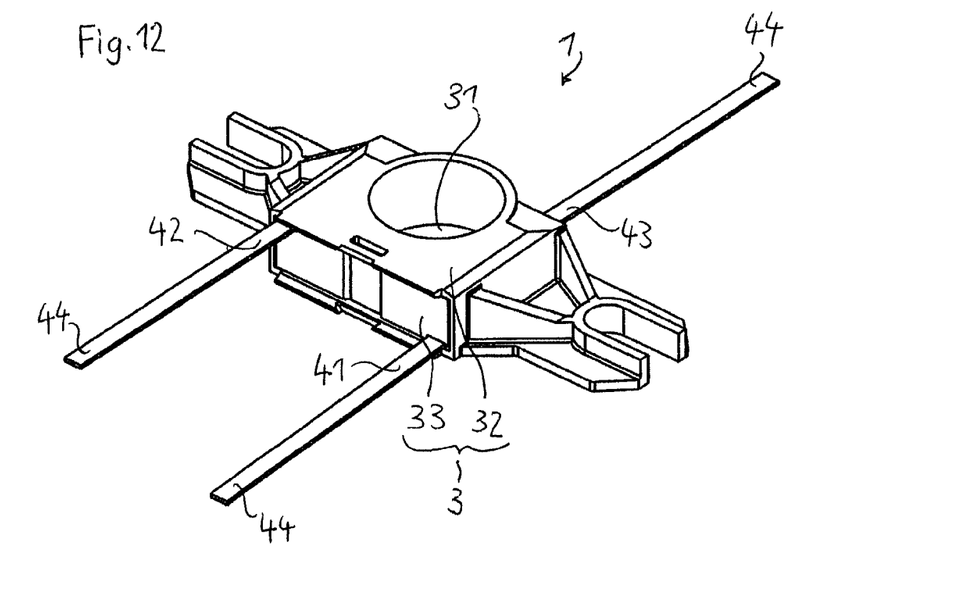

FIGS. 11 and 12 show schematic views of a heating module 1 according to a further example. FIG. 11 shows the heating module in the form of an exploded illustration, whereas FIG. 12 shows the heating module 1 in an assembled state.

According to this example, one of the two contact elements from the previous example is formed from two contact elements 42 and 43. The contact plate 42 and the contact plate 43 are arranged on the end face 24 of the PTC ceramic heating element 2.

In this case, the end face 24 of the PTC ceramic heating element 2 has two electrodes separated from one another and each formed by a metallization applied to the PTC ceramic heating element 2.

In addition to the contact lugs 44 of the contact plates 41, 42, the contact plate 43 has a connecting lug 44, which forms a third electrical contact of the heating module 1. By virtue of the three contact elements 41, 42, 43, the heating module 1 can be operated in two stages.

The heating modules in the examples shown in FIGS. 8 to 10 and FIGS. 11 and 12 can be used, for example, in a vaporization apparatus according to the example shown in FIGS. 6 and 7.

The heating modules 1 described here have few elements and, therefore, they can be produced and assembled easily and cost-effectively and, by virtue of the arrangement of the PTC ceramic heating element 2 close to and at least partially encompassing the opening in the housing, have a low power consumption.

Our modules and apparatus are not restricted to the examples by the description with reference thereto, but rather encompasses any novel feature and any combination of features.

The invention claimed is:

1. A heating module comprising:
   a housing with an opening;
   a PTC ceramic heating element arranged in the housing and having an inner face facing toward the opening, an outer face facing away from the opening and two end faces connecting the inner and outer faces; and
   three contact elements matched to the shape of the PTC ceramic heating element,
   wherein two contact elements are arranged on one end face of the PTC ceramic heating element, one contact element is arranged on the other end face of the PTC ceramic heating element, and the inner face is at least partially matched to the opening.

2. The heating module according to claim 1, wherein the PTC ceramic heating element is fastened between the contact elements by a clamp.

3. The heating module according to claim 1, wherein the contact elements are formed at least partially in an annular shape or at least partially in a U shape.

4. The heating module according to claim 1, wherein the contact elements comprise connecting lugs protruding out of the housing for the electrical contact-connection.

5. The heating module according to claim 1, wherein the end faces are at least partially beveled.

6. The heating module according to claim 1, wherein the PTC ceramic heating element is formed with an annular shape.

7. The heating module according to claim 6, wherein the PTC ceramic heating element is formed at least partially conically on the end faces.

8. The heating module according to claim 1, wherein the PTC ceramic heating element is formed in a U shape.

9. The heating module according to claim 8, wherein the PTC ceramic heating element has a smaller height on the inner face than on the outer face.

10. The heating module according to claim 1, wherein the housing comprises at least two housing parts connected to one another by a latching connection.

11. The heating module according to claim 10, wherein the at least two housing parts connect to a flanged inner sleeve.

12. The heating module according to claim 11, wherein the inner sleeve is arranged at least partially in the opening in the housing.

13. A vaporization apparatus comprising a container, liquid-conducting element and the heating module according to claim 1, wherein the liquid-conducting element protrudes into the heating module with one end and into the container with the other end.

14. The heating module according to claim 2, wherein the contact elements are formed at least partially in an annular shape or at least partially in a U shape.

15. The heating module according to claim 2, wherein the contact elements comprise connecting lugs protruding out of the housing for the electrical contact-connection.

16. The heating module according to claim 3, wherein the contact elements comprise connecting lugs protruding out of the housing for the electrical contact-connection.

\* \* \* \* \*